United States Patent [19]
Jones et al.

[11] Patent Number: 5,980,487
[45] Date of Patent: Nov. 9, 1999

[54] HYPODERMIC SYRINGE

[75] Inventors: Timothy Robert Jones, Godmanchester; Paul James Fearis, Cambridge, both of United Kingdom

[73] Assignee: Product Research Limited, United Kingdom

[21] Appl. No.: 08/737,348

[22] PCT Filed: May 4, 1995

[86] PCT No.: PCT/GB95/01017

§ 371 Date: Nov. 29, 1996

§ 102(e) Date: Nov. 29, 1996

[87] PCT Pub. No.: WO95/30446

PCT Pub. Date: Nov. 16, 1995

[30] Foreign Application Priority Data

May 4, 1994 [GB] United Kingdom .................. 9408773

[51] Int. Cl.$^6$ .................................................. A61M 5/00
[52] U.S. Cl. .......................... 604/110; 604/195; 604/218; 604/241
[58] Field of Search ..................................... 604/181, 187, 604/192, 195, 198, 218, 223, 224, 227, 240, 241, 243, 110; 128/919; 222/386, 390, 391

[56] References Cited

U.S. PATENT DOCUMENTS

| | | |
|---|---|---|
| 4,675,005 | 6/1987 | Deluccia . |
| 4,678,107 | 7/1987 | Ennis, III .............................. 604/228 |
| 4,790,822 | 12/1988 | Haining . |
| 4,810,249 | 3/1989 | Haber et al. .......................... 604/224 |
| 4,826,483 | 5/1989 | Molnar, IV ........................... 604/224 |
| 5,098,402 | 3/1992 | Davis . |
| 5,125,898 | 6/1992 | Kaufhold, Jr. et al. ................ 604/110 |
| 5,135,510 | 8/1992 | Maszkiewicz et al. ................ 604/195 |
| 5,242,419 | 9/1993 | Kiner et al. . |
| 5,256,151 | 10/1993 | Chul ...................................... 604/195 |
| 5,263,933 | 11/1993 | Novacek et al. ....................... 604/195 |

FOREIGN PATENT DOCUMENTS

| | | |
|---|---|---|
| 0327061 | 8/1989 | European Pat. Off. . |
| 0402908 | 12/1990 | European Pat. Off. . |
| 1454540 | 11/1976 | United Kingdom . |
| 2048077 | 12/1980 | United Kingdom . |
| 2266667 | 11/1993 | United Kingdom . |
| 9205820 | 4/1992 | WIPO . |
| 9209320 | 6/1992 | WIPO . |

*Primary Examiner*—Ronald K. Stright, Jr.
*Attorney, Agent, or Firm*—Galgano & Burke

[57] ABSTRACT

A syringe for the injection or taking of fluids having a needle mounting endpiece which is detachably coupled to barrel by mating features. A plunger and a coupled seal are guided by flanges sliding within guides and are further guided by protrusions so as to prevent rotation of the plunger and prevent unwanted contact between the flanges and the barrel. The plunger exhibits a bayonet-type fixture which upon rotation engages within the endpiece and allows retraction of the endpiece and coupled needle within barrel. Following engagement and retraction, the plunger may be prevented from movement by the engagement of protrusion on the barrel protrusions and abutment of radial protrusions against annular protrusions. Further embodiments and improvements are provided.

9 Claims, 11 Drawing Sheets

HYPODERMIC SYRINGE

FIELD OF INVENTION

This invention relates to hypodermic syringes and similar devices such as are utilised both for the injection of medicine into the body tissues of, and the taking of fluid samples from, human and animal patients. Thus it may also be applied to additional equipment requiring a similar function. It is particularly concerned with reducing the risk of cross infection through contact with or use of such syringes.

Disposable syringes are used throughout medicine and once used are usually discarded. However, the used needles are notoriously difficult to deal with; unsheathed they easily puncture bags and even when replaced within their originally sterile protective sheaths, they can fall out and present a hazard. This invention addresses the problems of inadvertent stick injuries caused to health workers with contaminated needles after use, particularly when they are being re-sheathed prior to disposal and, after disposal, to ancillary personnel such as cleaners, the prevention of unauthorised re-use of syringes and the ease of transportation of used devices.

BACKGROUND OF THE INVENTION

If problems such as those typified in the field of invention are to be overcome, needle and syringe combinations must be inexpensive to produce, easy to operate and should conform to applicable standards in order that they be widely utilised in the avoidance of such problems.

UK Patent Application GB 2 266 667 A describes such a combination wherein a standard needle is coupled to a detachable end-piece which is affixed to a syringe barrel. A flanged plunger which runs within guides integral to the barrel may, upon termination of use, be engaged into said endpiece by means of rotation in the manner of a bayonet type fixing. Having achieved engagement between said plunger and endpiece the combination is withdrawn within the barrel of the syringe thus shielding the needle.

This system suffers from the fact that as the plunger may be repeatedly moved to the extremes of axial travel allowing both the intake and expulsion of fluids, an unavoidable volume ('dead-space') of unexpelled fluid is inevitable since a further rotary motion is required in order to engage to the endpiece and there is also no means provided of evacuating fluid from within the central bore of the endpiece. It may be noted that such a dead-space is undesirable and, whilst this cannot be completely eliminated, it is preferred that this unexpelled volume be minimised.

Furthermore this syringe requires that both the plunger and endpiece are sealed to the barrel in order to eliminate the leakage of fluid. This is achieved by the use of separate compressible sealing components which are captured between the components to be sealed. Whilst the same compressible component is utilised twice to serve this purpose, there is undesirable additional cost associated with this solution.

Additionally it may be noted that this syringe utilises an annulus of perforations which are required to break or tear tangentially upon rotation of the plunger. This requires that the detachable portion of the endpiece and its support structure are formed integrally to each other as one component.

The device is such that tearing force occurs in one direction and in one plane. It has been observed that this single action does not provide the optimum method of breaking the perforations or initiating the withdrawal of the plunger/endpiece/needle. Furthermore it is identified that components incorporating such break-off features are sometimes difficult and expensive to develop and may exhibit varying properties which may affect their performance.

Additionally, whilst the syringe provides a means of attaching the plunger/endpiece/needle combination to the barrel upon full retraction of the needle, there is little to inhibit the complete withdrawal of this combination from the barrel component, whereupon it would be re-exposed. In this eventuality the needle is once again undesirably exposed and/or subject to interference.

GB 2 266 667 A represents the closest prior proposal currently known to the applicant and the present invention was developed from it. Also known to the applicant, however, and disclosed herein for the record, are the following published patent specifications:

| | |
|---|---|
| GB 1454540 | GB 2048077 |
| US 4790822 | US 5098402 |
| EP 0327061 | EP 0402908 |
| WO 92/05820 | WO 92/09320 |

Additionally, U.S. Pat. No. 5,242,419 discloses a syringe formed from a barrel having internal righthand threads at each end, a plunger which supports a piston near one end, and a tapered distal end provided with a lefthand thread. The needle has a cap with an internal lefthand thread and a flange configured to engage the internal threads of the barrel.

U.S. Pat. No. 4,675,005 is directed towards a disposable syringe having a locking device so that after use, a hub and cannula of the syringe can be detached from the cylindrical body, withdrawn thereinto, and locked thereto.

SUMMARY OF THE INVENTION

In view of the above considerations, it is therefore the aim of the present invention to provide a disposable hypodermic syringe which, through an ability to enable retraction of used needles within the barrel and allow coupling of retracted needle and plunger to the barrel, reduces the aforementioned risks and, through the incorporation of a number of detailed design features, overcomes the problems with existing designs of improved hypodermic syringes identified above.

The invention provides a hypodermic syringe, of a kind known generally per se and comprising a barrel, a plunger and a needle-receiving endpiece, with guide means mounting the plunger slidably within said barrel so as to define a fluid chamber, and support means locating said endpiece at least partially within said barrel to receive said needle in use; the plunger—again in a manner previously proposed per se—being normally prevented by the guide means from rotating as it travels linearly down the barrel to expel the fluid through the needle, but being freed from such preventative means when it reaches its fully-depressed state; the arrangement being characterised by the provision of appropriately profiled inter engaging surfaces formed respectively on the exterior of said plunger and the interior of said barrel, whereby cooperation of said inter engaging surfaces during rotation of said plunger when in its fully depressed state causes an automatic and relatively slight axial retraction of said plunger such that the pressure in said fluid chamber is reduced, thereby tending automatically to draw any residual fluid away from the tip of said needle and back into said fluid chamber.

Preferably said appropriately profiled inter engaging surfaces comprise at least one angled face located at the needle-remote end of said barrel and at least one radial protrusion located in that region of said plunger which lies adjacent said angled face when the plunger reaches its fully depressed state.

The invention also encompasses a syringe as outlined above and wherein a finger protrudes from said plunger towards and ultimately—as the plunger approaches the endpiece in its fluid expelling travel—into a complementary recess formed in said endpiece; characterised by the features that the progressive entry of said finger into said recess acts so as to reduce the so-called dead space—the volume of unexpelled fluid—within said chamber and in that neither the finger nor the recess acts to inter engage said plunger with said endpiece at any point during such entry.

Preferably said endpiece carries a sealing member which seals against the interior of said barrel so as to substantially prevent leakage of fluid from said fluid chamber, characterised in that the sealing member is formed integrally with said endpiece and in that the sealing member exhibits in cross-section a flanged profile in which a gap is clearly visible between the barrel-contacting region of the seal and the rest of the endpiece of which the sealing member forms an integral part.

Preferably also said sealing member is of a double-lipped construction in which two concentric and substantially annular projections form the seal with the interior surface of said barrel and said projections whilst being visibly separately defined are closely adjacent one another.

Where a screw-threaded inter engagement between the needle and the endpiece is provided to reduce the chances of inadvertent separation of the needle from the endpiece the thread is preferably formed on a tapered surface and is thus a spiral thread.

Advantageously the crests of said thread when viewed in cross-section are substantially flat.

The roots of said thread when viewed in cross-section may be of a non-flat and preferably non-vee cross-section.

In a preferred arrangement wherein said endpiece further comprises a number of recesses, each of which is interlockable with a corresponding one of a number of protrusions on the interior surface of said barrel, each of said recesses and protrusions is an annular recess and annular protrusion respectively, the disposition and inter engagement of said recesses and protrusions is such that said endpiece is held within said barrel, before and during use, so as to substantially prevent unwanted movement therebetween and said recesses and protrusions allow said endpiece to be axially slidable within said barrel after use.

The invention includes specifically within its scope syringes substantially as described herein with reference to and as illustrated in the accompanying drawings, since these constitute currently the best ways known to the applicant of putting the invention into practice.

BRIEF DESCRIPTION OF THE DRAWINGS

Four specific embodiments of the invention will now be described by way of example with reference to the accompanying drawings in which.

DESCRIPTION OF THE PREFERRED EMBODIMENTS

Figure 1:
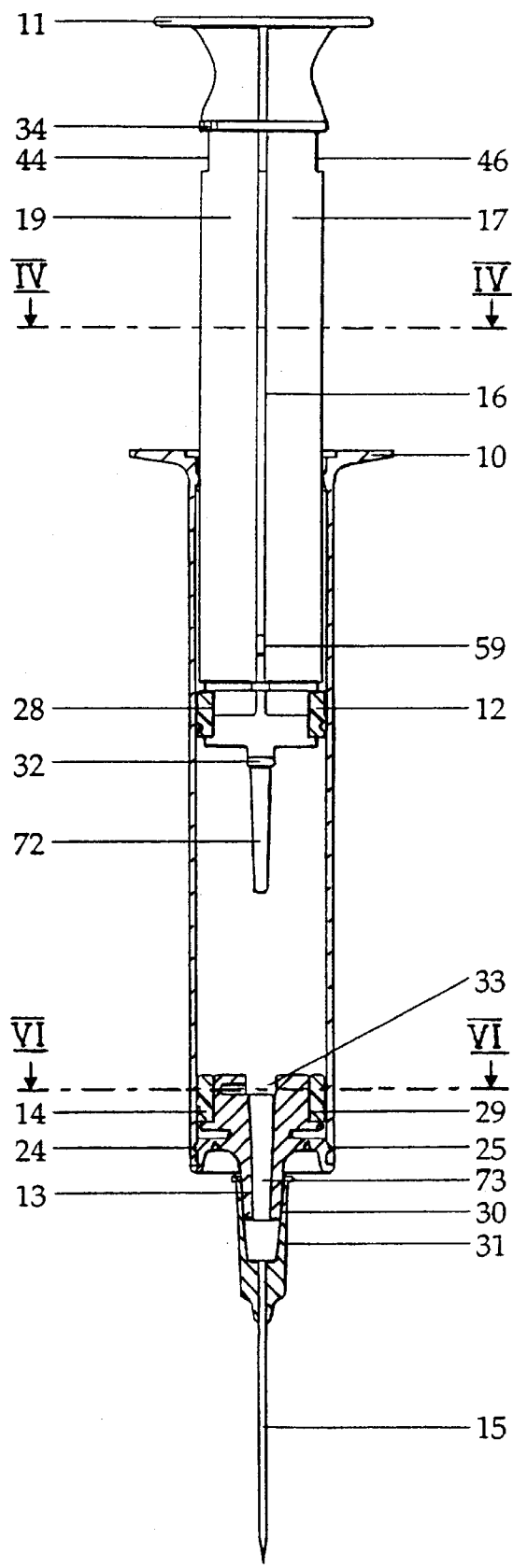
FIG. 1 is a side view, partly in section, of a syringe assembly embodying the present invention, orientated to allow use for withdrawal and injection of fluids.
Figure 2:
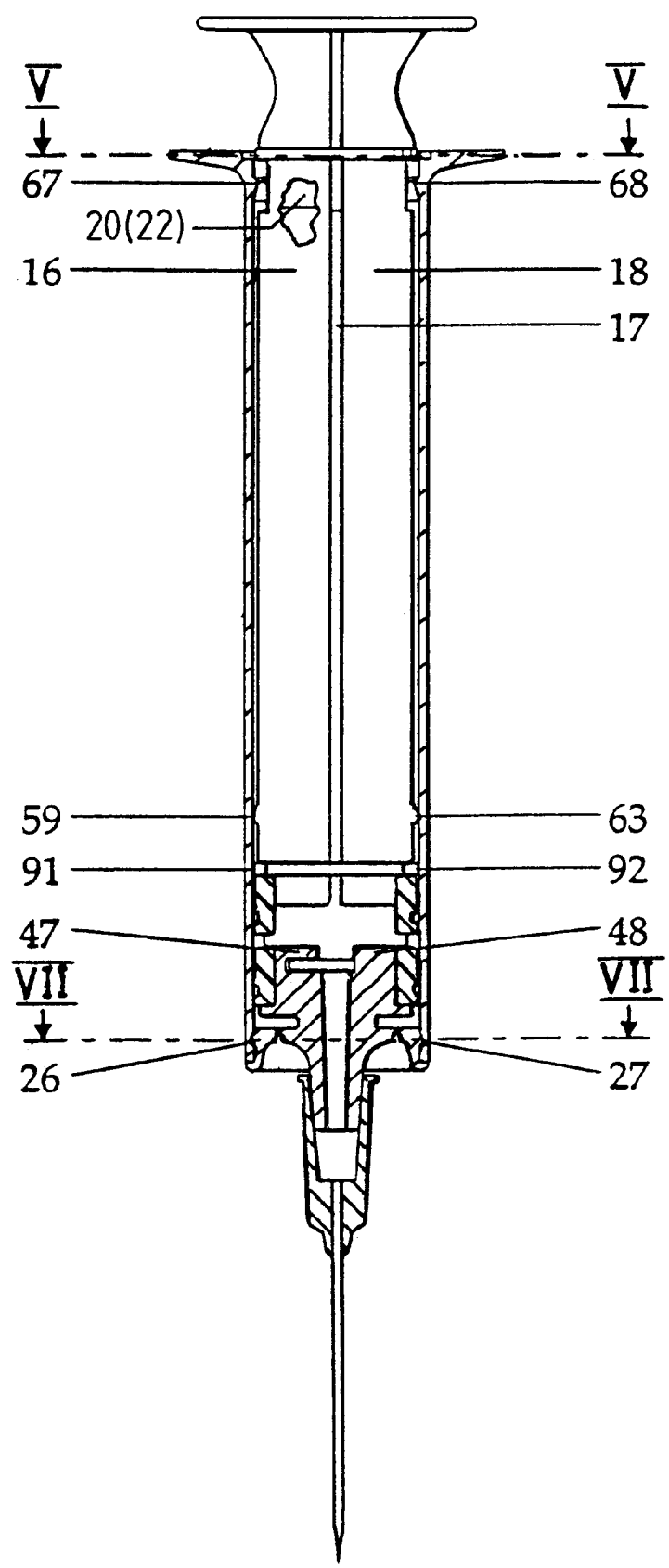
FIG. 2 is a side view, partly in section, of the assembly shown in FIG. 1 orientated to provide coupling between plunger and endpiece.
Figure 3:
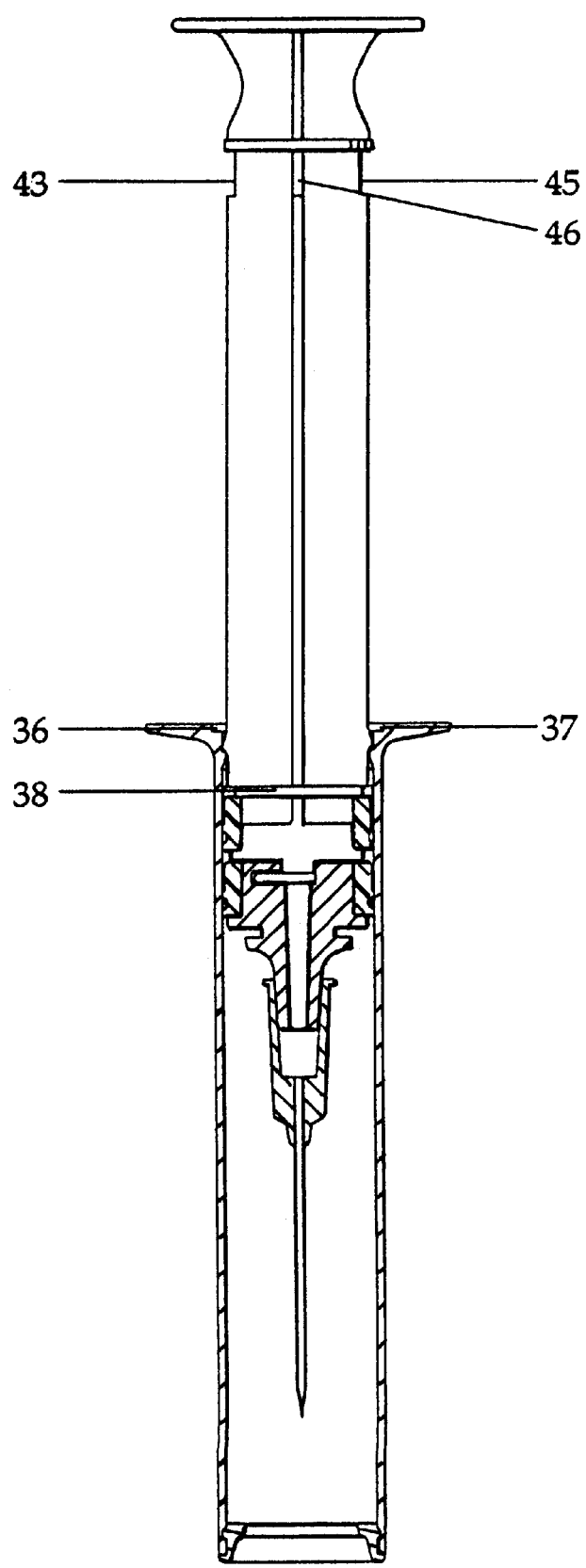
FIG. 3 is a side view, partly in section, of the assembly shown in FIGS. 1 and 2 with plunger, coupled section of endpiece and hypodermic needle withdrawn inside the barrel and coupling provided between plunger and barrel so as to inhibit further motion.
Figure 4:
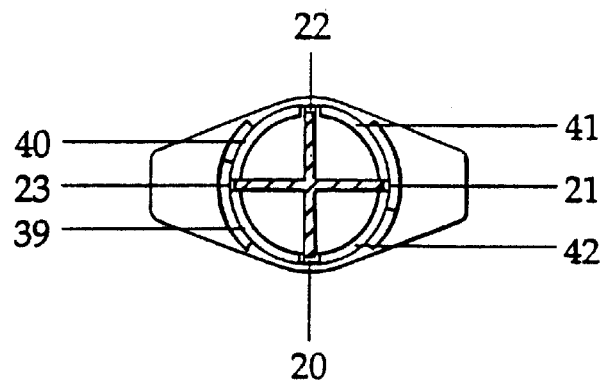
FIG. 4 is a section through line AA of FIG. 1.
Figure 5:
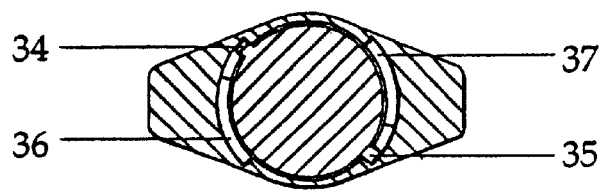
FIG. 5 is a section through line BB of FIG. 2.
Figure 6:
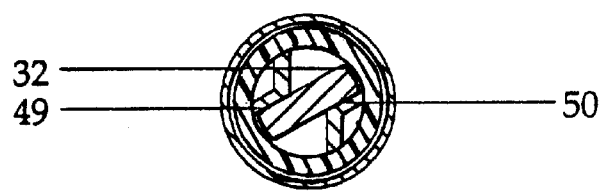
FIG. 6 is a section through line CC of FIG. 1.
Figure 7:
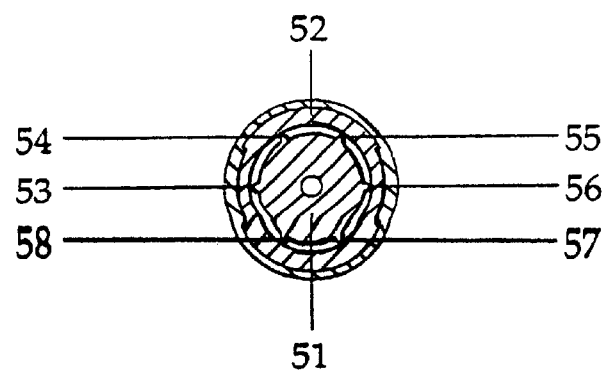
FIG. 7 is a section through line DD of FIG. 2.
Figure 8:
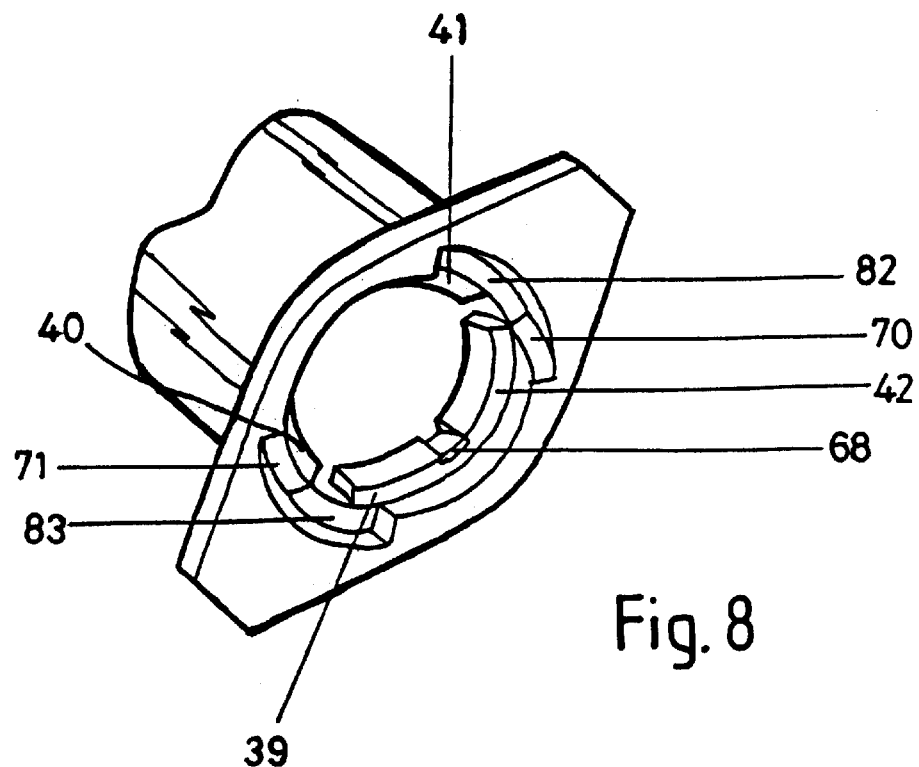
FIG. 8 shows in perspective the upper end of the barrel shown in FIGS. 1, 2 and 3.
Figure 9:
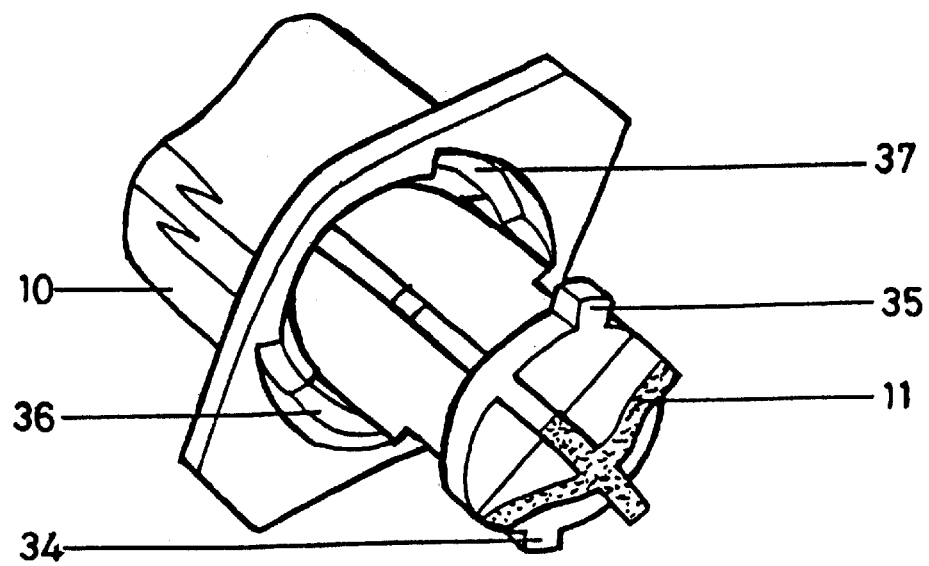
FIG. 9 shows in perspective, partly in section, the upper end of the barrel and the plunger shown in FIGS. 1, 2 and 3.

Referring to FIGS. 1 to 9, a plunger 11 slides within a barrel 10, flanges 16, 17, 18 and 19 sliding within guides 20, 21, 22 and 23 respectively to prevent rotation of the plunger within the barrel 10. An a elastomeric seal 12, located in annular groove 28, provides a watertight seal between the plunger 11 and the barrel 10. Flanges 16, 17, 18, 19 extend along substantially the whole length of plunger 11. Guides 20, 21, 22, 23 extend downwardly from the "top end" of barrel 10 (i.e the end furthest from the needle 15) to approximately 5 mm below the top end of barrel 10.

An endpiece 13 is coupled to the barrel 10 by means of projections 24 and 25 fitting into corresponding annular grooves 26 and 27. Endpiece 13 comprises an annular ring section 52 (see FIG. 7) and an "engaged section" 51 which is adapted to engage a standard hypodermic needle 15. The two sections 51 and 52 are integrally formed, with engaged section 51 being attached to annular ring section 52 by means of moulding details 53–58. An elastomeric seal 14 located in annular groove 29 provides a watertight seal between the endpiece 13 and the barrel 10. A taper 30 provides coupling with the internal taper 31 of a standard hypodermic needle 15.

Under normal use, the plunger 11 slides within barrel 10 with bayonet 32 moving within channel 33 at the bottom of travel and further travel is prevented by means of radial protrusions 34 and 35 locating within annular grooves 36 and 37 respectively.

When plunger 11 is at the bottom of travel and bayonet 32 resides within channel 33, the dead-space of unexpelled fluid is minimised by protruding circular finger 72 mounted on plunger 11 passing down bore 73 thus displacing fluid. The fit between finger 72 and bore 73 is such that the volume of fluid displaced is maximised but coupling does not occur.

Significantly, the relationship between circular finger 72 and bore 73 is not used as a means of engagement between plunger 11 and endpiece 13 (this being achieved by means of the bayonet 32 described below). The circular finger 72/bore 73 arrangement serves to reduce the volume of unexpelled fluid i.e the significant problem of "dead-space" within the fluid chamber.

In addition, radial protrusions 67 and 68 in combination with guides 20, 21, 22 and 23 on barrel 10 also provide guidance for the edges of flanges 17 and 19 and, by virtue of this, maintain clearance and inhibit contact between flanges 16, 17, 18 and 19 and the inside face of barrel 10.

Complete withdrawal of plunger 11 from within barrel 10 during use is inhibited by seal 12 being of such a design so as to be unable to pass annular protrusions 39, 40, 41 and 42 without significant force to overcome the interference between seal 12 and the protrusions 39, 40, 41 and 42.

After use plunger 11 slides within barrel 10 to the bottom of travel with radial protrusions 34 and 35 locating within annual grooves 36 and 37 respectively, bayonet 32 locates within channel 33 and circular finger 72 locates within bore 73. At the bottom of travel, flanges 16–19 have passed guides 20–23 and thus the plunger 11 is able to be rotated. Plunger 11 is rotated with annular protrusions 39, 40, 41 and 42 passing through recesses 43, 44, 45 and 46 respectively whilst radial protrusions 34 and 35 moving within annular grooves 36 and 37 restrict the degree of rotation of plunger 11 within barrel 10. During rotation, bayonet 32 engages endpiece 13 by moving under overhangs 47 and 48 and abutting against walls 49 and 50. Within this first sector of rotation of plunger 11 within barrel 10 and consequent rotation of radial protrusions 34 and 35 within annular grooves 36 and 37, protrusions 34 and 35 run along faces 82 and 83 of annular grooves 36 and 37. The remaining sector of rotation of plunger 11 within barrel 10 causes engaged section 51 of endpiece 13 to break away from annular ring section 52 of endpiece 13 through shearing of breakaway moulding details 53, 54, 55, 56, 57 and 58. This rotational shearing is augmented and improved upon by axial shearing induced by protrusions 34 and 35 being forced to rise up angled faces 70 and 71, thus imparting an axial load upon plunger 11 and engaged section 51 of endpiece 13.

Separation of endpiece 13 is thus improved by this additional axial force. The additional axial force has the important effect of reducing the pressure within the fluid chamber and/or needle as the plunger 11 is slightly withdrawn as a result of the above-mentioned axial force. This reduction in pressure tends to draw any residual (and potentially contaminated) fluid back into the syringe (i.e away from the end of needle 15) and thus significantly reduces the risk of fluid "spurting" or leaking from the needle 15 during the retraction process.

Plunger 11 is partially withdrawn out of barrel 10 with flanges 16, 17, 18 and 19 sliding within guides 23, 20, 21 and 22 respectively, and engaged section 51 of end piece 13 and coupled hypodermic needle 15 being simultaneously withdrawn inside barrel 10.

Towards the extreme of sliding travel of plunger 11 within barrel 10, radial protrusion 59 on flange 16 and radial protrusion 63 on flange 18 pass and engage radial protrusions 67 and 68 of barrel 10, thus inhibiting further movement of plunger within barrel 10. Furthermore radial protrusions 91 and 92 on plunger 11 abut against annular protrusions 39, 40, 41 and 42 at the endpiece engaging end 38 of the barrel 10 inhibiting further withdrawal of plunger/needle.

Figure 10:
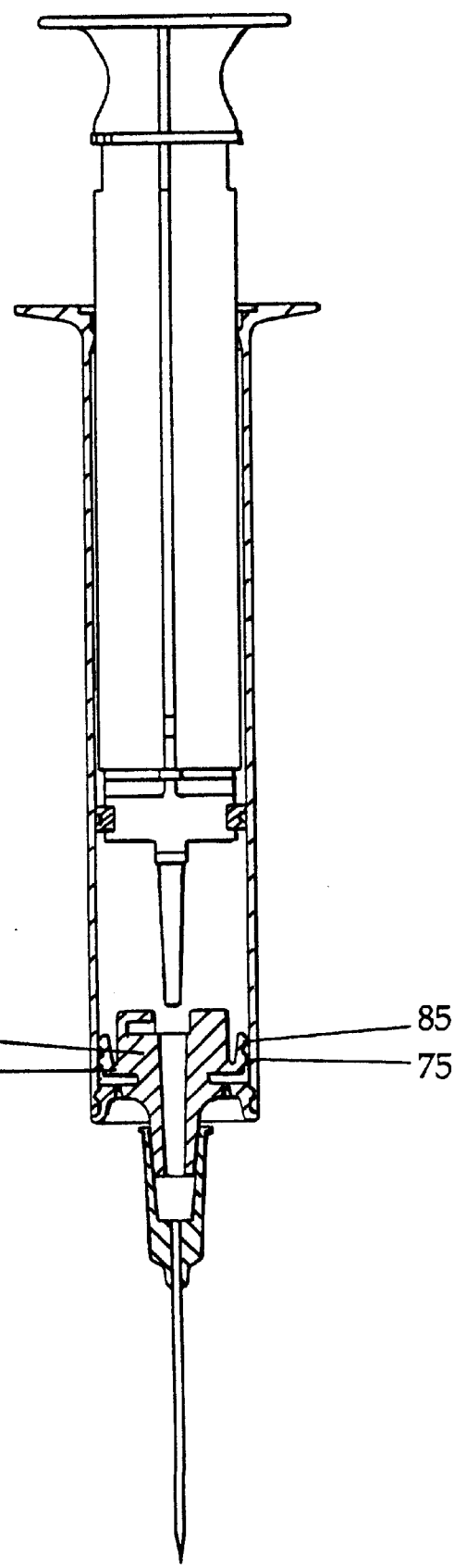
FIG. 10 is a side view, partly in section, of a syringe assembly embodying the present invention as shown in FIG. 1 with an improved design of endpiece exhibiting an integrally moulded sealing means, orientated such as to allow use in a device for the withdrawal and injection of fluids.
Figure 11:
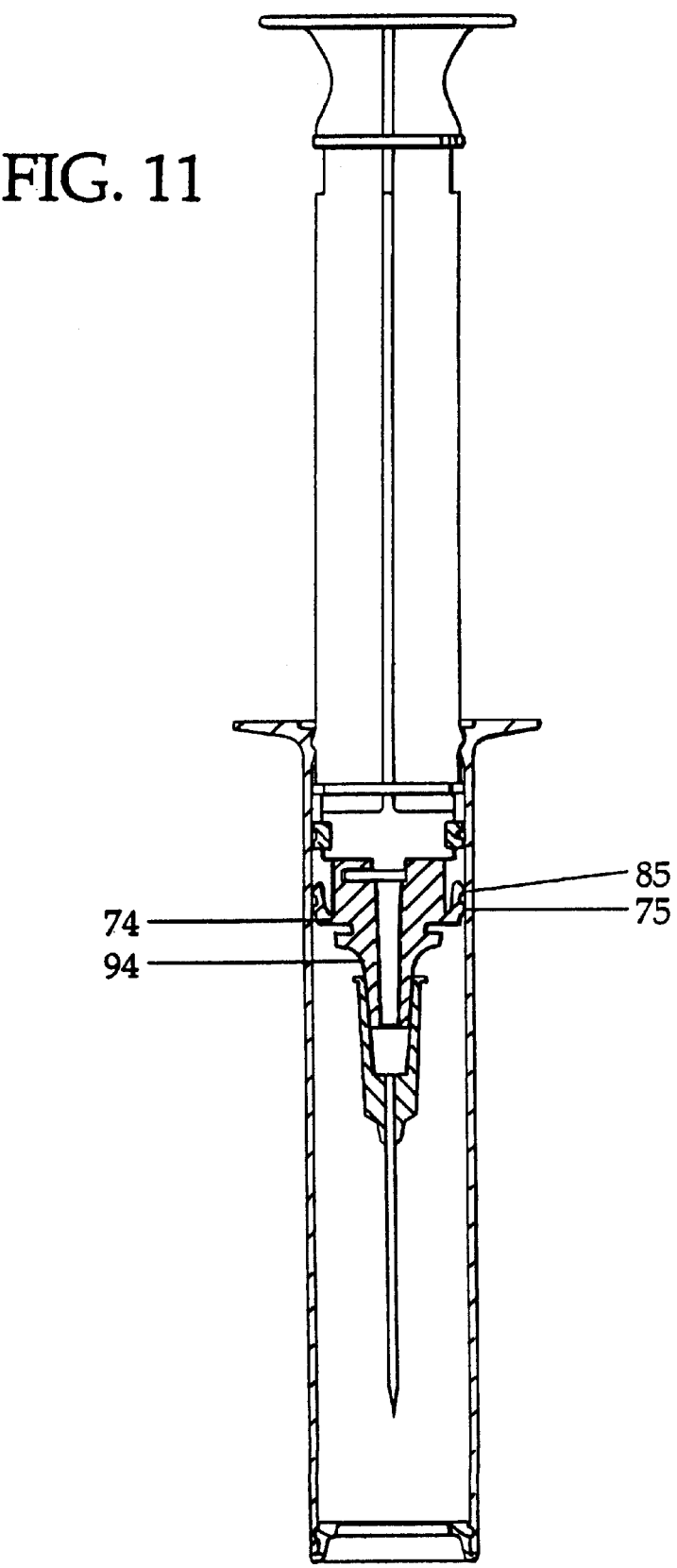
FIG. 11 is a side view, partly in section, of the assembly shown in FIG. 10 with plunger, coupled endpiece and hypodermic needle withdrawn inside the barrel and coupling provided between plunger and barrel so as to inhibit further motion.

Referring to FIGS. 1, 10 and 11 a second embodiment of the invention is shown. An endpiece 84 provides an improvement upon endpiece 13 within barrel 10. Endpiece 84 improves upon endpiece 13 by exhibiting an integral sealing member 74 which may carry sealing beads 75 and 85 in order to augment its performance and thus eliminating the requirement for elastomeric sealing device 14. Sealing member 74 may be caused to provide a radial force against barrel 10 inhibiting the flow of fluid past the endpiece 84. FIG. 11 illustrates such an embodiment of this sealing device in the retracted position with needle 15 positioned within barrel 10, central section 94 of endpiece 84 having moved by sliding within barrel 10.

Use of the integral sealing member 74 simplifies the construction of the syringe, thus reducing production costs.

Figure 12:
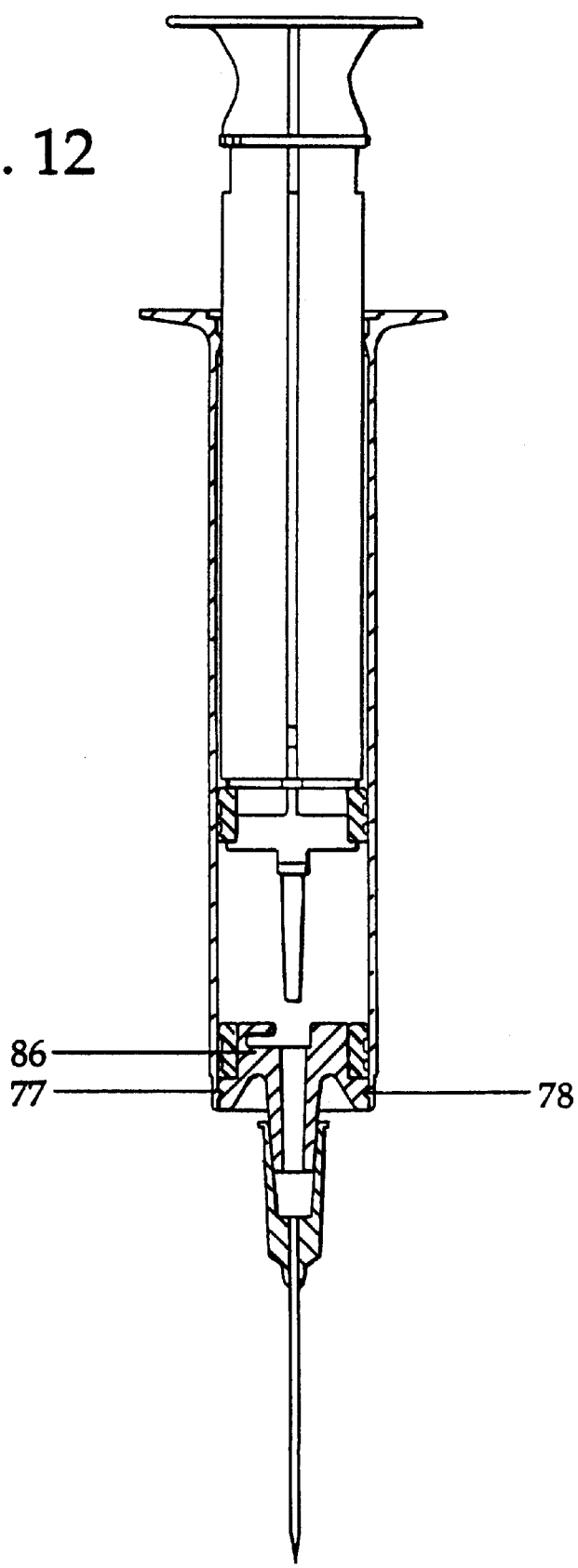
FIG. 12 is a side view, partly in section, of a third syringe assembly embodying the present invention as shown in FIG. 1 with an improved design of endpiece, orientated such as to allow use in a device for the withdrawal and injection of fluids.
Figure 13:
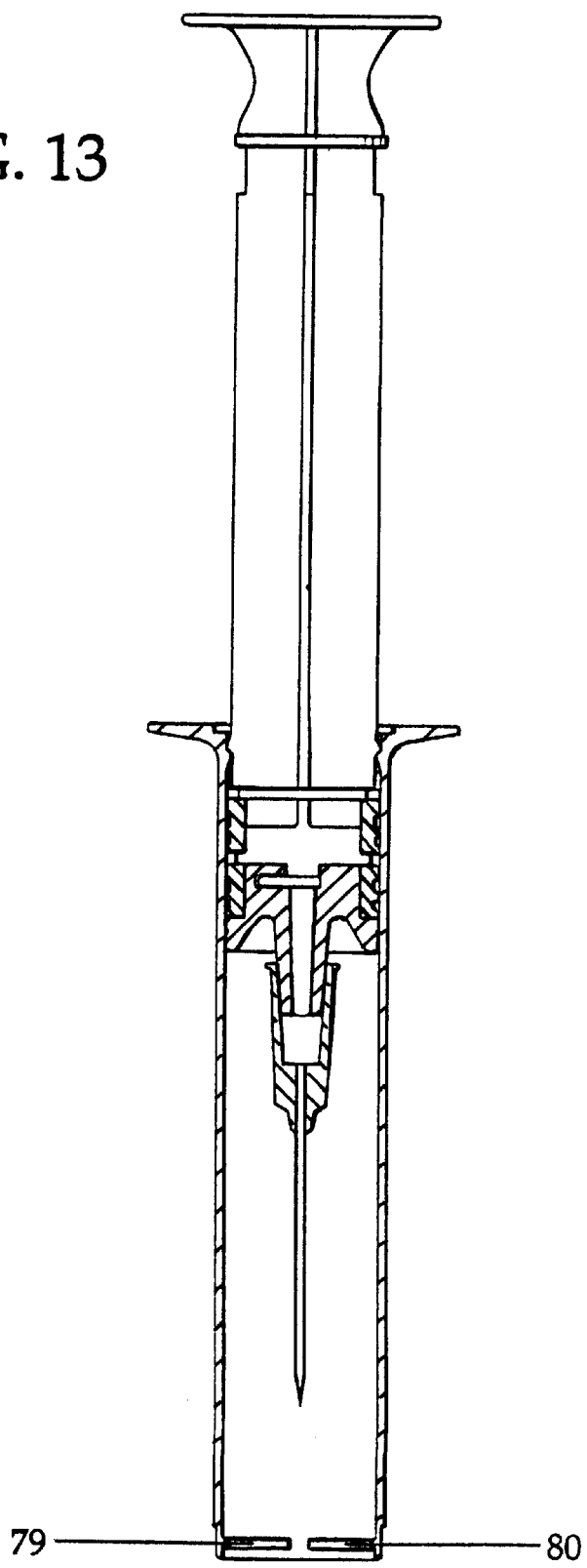
FIG. 13 is a side view, partly in section, of the assembly shown in FIG. 12 with plunger, coupled endpiece and hypodermic needle withdrawn inside the barrel and coupling provided between plunger and barrel so as to inhibit further motion.

Referring to FIGS. 1, 12 and 13, a third embodiment of the invention is shown. An endpiece 86 provides an improvement upon endpiece 13 within barrel 10. Endpiece 86 improves upon endpiece 13 by exhibiting annular recesses 77 and 78 which interlock with annular protrusions 79 and 80 on barrel 10. By so doing endpiece 86 is coupled to and held by barrel 10 in such a manner so as to prevent unwanted movement and inhibit removal during normal use but, after use and following engagement of bayonet 32 under overhangs 47 and 48, allow endpiece 86 to slide within barrel 10. By so doing endpiece 86 remains intact and is not required to exhibit, nor separate from, restraining means 53, 54, 55, 56, 57 and 58 as present in endpiece 13.

Figure 14:
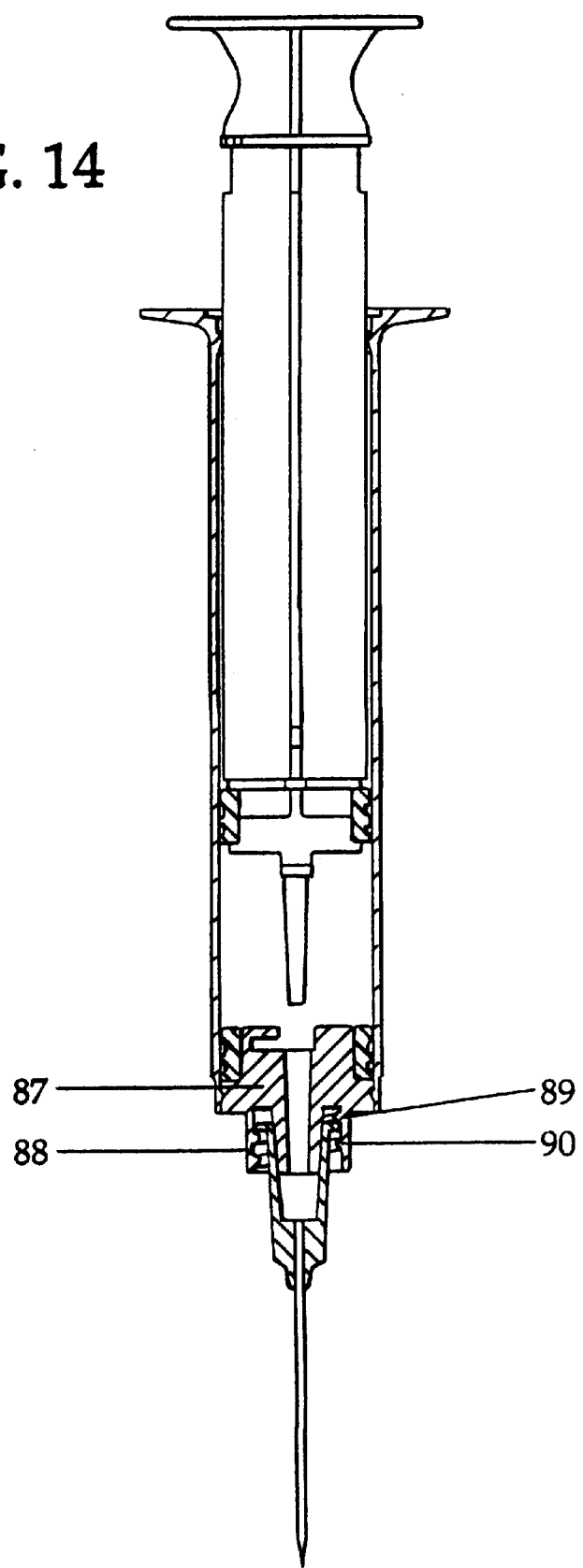
FIG. 14 is a side view partly in section of a fourth syringe assembly embodying the present invention as shown in FIG. 1 with an improved design of endpiece incorporating improved needle retention, orientated such as to allow use in a device for the withdrawal and injection of fluids.
Figure 15:
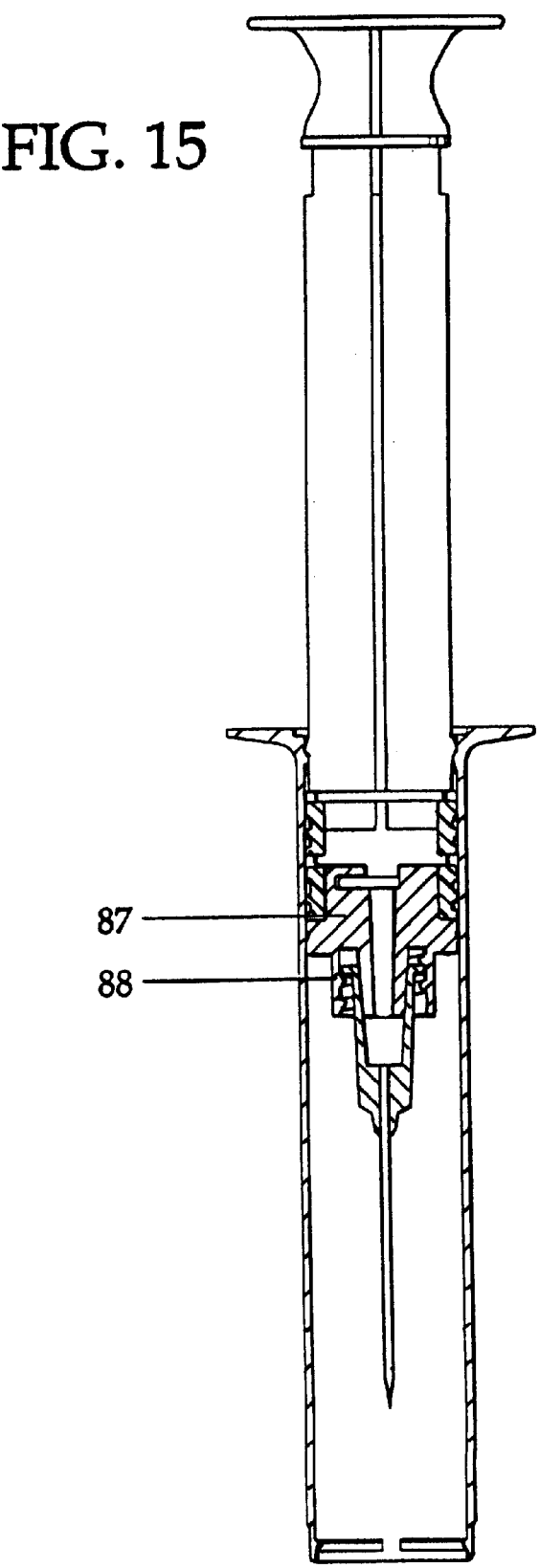
FIG. 15 is a side view, partly in section, of the assembly shown in FIG. 14 with plunger, coupled endpiece and hypodermic needle withdrawn inside the barrel and coupling provided between plunger and barrel so as to inhibit motion.

Referring to FIGS. 14 and 15 a fourth embodiment of the invention is shown. An endpiece 87, similar in design to endpiece 86, exhibits an additional annular flange 88 with a number of raised protrusions 89 and 90 on its inner face. These protrusions spiral in the manner of a threaded component in order to allow the engagement of two radial protrusions frequently found on taper fitting needles. Once engaged in the spiral the needle may be more securely coupled to the taper, endpiece and syringe by rotation of the needle causing the needle protrusions to move along the axis of the spiral.

FIGS. 14 and 15 show that the crests of the thread (when viewed in cross-section) are substantially flat, while the roots of the thread are of a non-flat, in this example curved, cross-sectional profile.

The present invention and embodiments thus provide improved methods of coupling of plunger to needle and withdrawal of needle within barrel, thus sheathing the needle and reducing the possibility of accidental stabbing and, also in addition through coupling of withdrawn plunger and barrel, a means of preventing re-use.

We claim:

1. A hypodermic syringe comprising:
   a barrel;
   a plunger;
   a needle;

a frangible endpiece for receiving said needle;

support means locating said endpiece at least partially within said barrel to receive said needle in use, guide means mounting the plunger slidably within said barrel, so as to define a fluid chamber; said guide means having preventative means for normally preventing said guide means from rotating as it travels linearly down the barrel so as to expel fluid through the needle but said plunger being freed from such preventative means when it reaches its fully depressed state; and means for causing automatic and relatively slight axial retraction of said plunger such that the pressure in said fluid chamber is reduced, whereby tending automatically to draw any residual fluid away from the tip of said needle and back into said fluid chamber, said means including appropriately profiled inter engaging surfaces formed respectively on the exterior of said plunger and on the interior of said barrel, which cooperate during rotation of said plunger when in its fully depressed state to effect said slight axial retraction of said plunger and which assist the frangible break-off of the endpiece.

2. The syringe as claimed in claim 1, wherein said endpiece carries a sealing member which seals against the interior of said barrel so as to substantially prevent leakage of fluid from said fluid chamber, characterized in that the sealing member is formed integrally with said endpiece and in that the sealing member exhibits in cross-section a flanged profile in which a gap is clearly visible between the barrel-contacting region of the seal and the rest of the endpiece of which the sealing member forms an integral part.

3. The syringe as claimed in claim 2, wherein said sealing member is of a double-lipped construction in which two concentric and substantially annular projections form the seal with the interior surface of said barrel and in that said projections whilst being visibly separately defined are closely adjacent one another.

4. The syringe as claimed in claim 1, wherein a screw-threaded inter engagement between the needle and the endpiece is provided to reduce the chances of inadvertent separation of the needle from the endpiece characterized in that the thread is formed on a tapered surface and is thus a spiral thread.

5. The syringe according to claim 4, wherein said thread has crests which when viewed in cross-section are substantially flat.

6. The syringe as claimed in claim 4, wherein said thread has roots which when viewed in cross-section are of a non-flat and non-vee cross-section.

7. The syringe as claimed in claim 1, wherein said appropriately profiled inter engaging surfaces comprise at least one angled face located at the end of said barrel remote from said needle and at least one radial protrusion located in that region of said plunger which lies adjacent said angled face when the plunger reaches its fully depressed state.

8. The syringe as claimed in claim 1, wherein a finger protrudes from said plunger towards and ultimately—as the plunger approaches the endpiece in its fluid expelling travel—into a complementary recess formed in said endpiece; characterized in that the progressive entry of said finger into said recess acts so as to reduce "dead space"—the volume of unexpelled fluid—within said chamber and in that neither the finger nor the recess acts to inter-engage said plunger with said endpiece at any point during such entry.

9. The syringe as claimed in claim 1, wherein said endpiece further comprises a number of recesses, each of which is interlockable with a corresponding one of a number of protrusions on the interior surface of said barrel, characterized in that each of said recesses and protrusions is an annular recess and annular protrusion respectively, the disposition and inter engagement of said recesses and protrusions being such that said endpiece is held within said barrel, before and during use, so as to substantially prevent unwanted movement therebetween, and in that said recesses and protrusions allow said endpiece to be axially slidable within said barrel after use.

\* \* \* \* \*